(12) United States Patent (10) Patent No.: US 8,083,643 B2
Ng et al. (45) Date of Patent: Dec. 27, 2011

(54) SYSTEMS AND METHODS FOR ACCESSING PERSONALIZED FITNESS SERVICES USING A PORTABLE ELECTRONIC DEVICE

(75) Inventors: Stanley Carl Ng, Los Altos, CA (US); Michael Hailey, Campbell, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 12/605,582

(22) Filed: Oct. 26, 2009

(65) Prior Publication Data

US 2011/0098156 A1 Apr. 28, 2011

(51) Int. Cl.
*A63B 71/00* (2006.01)
*G06Q 30/00* (2006.01)

(52) U.S. Cl. .......................... 482/1; 705/14.1

(58) Field of Classification Search ...... 482/1, 901–902, 482/2–9; 700/91–93; 705/2–4, 14.1–14.39, 705/26, 319, 26.1; *A63B 71/00; G06Q 30/00*
See application file for complete search history.

(56) References Cited

U.S. PATENT DOCUMENTS

| | | |
|---|---|---|
| 5,390,281 A | 2/1995 | Luciw et al. |
| 5,434,777 A | 7/1995 | Luciw |
| 5,477,447 A | 12/1995 | Luciw et al. |
| 5,608,624 A | 3/1997 | Luciw |
| 5,621,903 A | 4/1997 | Luciw et al. |
| 5,625,814 A | 4/1997 | Luciw |
| 5,644,735 A | 7/1997 | Luciw |
| 5,721,845 A | 2/1998 | James et al. |
| 5,864,844 A | 1/1999 | James et al. |
| 5,978,766 A | 11/1999 | Luciw |
| 7,643,895 B2 | 1/2010 | Gupta et al. |
| 2002/0120511 A1 | 8/2002 | Hanes |
| 2003/0009376 A1 | 1/2003 | Ekstrom |
| 2005/0164833 A1 | 7/2005 | Florio |
| 2006/0025282 A1 | 2/2006 | Redmann |
| 2006/0143214 A1* | 6/2006 | Teicher ........................ 707/101 |
| 2006/0205564 A1* | 9/2006 | Peterson .......................... 482/8 |
| 2007/0271116 A1 | 11/2007 | Wysocki et al. |
| 2008/0071794 A1 | 3/2008 | Barnard |
| 2008/0077620 A1 | 3/2008 | Gilley et al. |
| 2008/0262928 A1* | 10/2008 | Michaelis ....................... 705/14 |
| 2009/0012925 A1* | 1/2009 | Brown ........................... 706/46 |
| 2009/0076903 A1* | 3/2009 | Schwarzberg et al. ......... 705/14 |
| 2009/0170480 A1 | 7/2009 | Lee |
| 2009/0181826 A1* | 7/2009 | Turner .............................. 482/4 |

(Continued)

OTHER PUBLICATIONS

Linton Freeman, The Development of Social Network Analysis. Vancouver: Empirical Press, 2006 (via Wikipedia: http://en.wikipedia.org/wiki/Social_network).*

(Continued)

*Primary Examiner* — Stephen Crow
*Assistant Examiner* — Oren Ginsberg
(74) *Attorney, Agent, or Firm* — Kramer Levin Naftalis & Frankel LLP

(57) ABSTRACT

This is directed to systems and methods for accessing personalized fitness services through an integrated application available to a portable electronic device. The integrated application can provide a full fitness center experience by introducing potential new customer to a fitness center and then motivating them to return to the fitness center as active members. For example, the integrated application can provide functions to introduce new customers to a fitness center, can provide functions to motivate customers to join and actively visit the fitness center, can provide in-gym motivation, and can provide post-workout motivation.

22 Claims, 8 Drawing Sheets

U.S. PATENT DOCUMENTS

| | | | |
|---|---|---|---|
| 2009/0221404 A1 | 9/2009 | Dorogusker et al. | |
| 2009/0258758 A1* | 10/2009 | Hickman et al. | 482/8 |
| 2009/0267783 A1 | 10/2009 | Vock et al. | |
| 2010/0056341 A1* | 3/2010 | Ellis et al. | 482/9 |
| 2010/0062818 A1 | 3/2010 | Haughay, Jr. et al. | |
| 2010/0062905 A1 | 3/2010 | Rottler et al. | |
| 2010/0179028 A1* | 7/2010 | Watterson et al. | 482/9 |
| 2010/0197463 A1 | 8/2010 | Haughay, Jr. et al. | |

OTHER PUBLICATIONS

Lara Hale, "Fitness Clubs Use Mobile Apps to Interact with Members and Prospects", Mar. 1, 2011, http://clubindustry.com/forprofits/fitness-club-mobile-apps-connect-members-and-propects-20110301/index1.html.*

Bryan O'Rourke, How Mobile Devices Will Affect the Health Club Industry, Feb. 7, 2011, http://clubindustry.com/stepbystep/clubs/mobility-affect-clubs-20110207/.*

Sala, P., Traver, M., Traver, V., Guillën, S., and Dapcich, J.M. (2006) *Virtual Trainer Using Smart Wearable Devices*. http://www.hitech-projects.com/euprojects/myheart/.

24 Hour Fitness Classes, http://www.24hourfitness.com/classes/schedules/, accessed Sep. 1, 2010.

YMCA News & Events, http://www.missionvalley.ymca.org/general-information/news.html, accessed Sep. 1, 2010.

* cited by examiner

SYSTEMS AND METHODS FOR ACCESSING PERSONALIZED FITNESS SERVICES USING A PORTABLE ELECTRONIC DEVICE

FIELD OF THE DISCLOSURE

This is directed to accessing personalized fitness services through a portable electronic device.

BACKGROUND OF THE DISCLOSURE

The benefits of exercise and healthy living are well-known in present day society. To this end, it is not uncommon for people to aspire to regularly workout or go to a fitness center. However, despite a person's good intentions or his desire to workout, a person may not achieve their goal amount of exercise. For example, busy schedules, not knowing how to properly use gym equipment, or other factors can cause a person to lack the motivation to go to a fitness center and workout.

To help become motivated to regularly visit a fitness center, people often resort to techniques such as finding a workout buddy, scheduling sessions with a fitness trainer, attending workout classes, and the like. However, although these approaches for becoming motivated can be serviceable, they remain disjointed, lack a central hub, and may still result in the person losing motivation (e.g., the person may nonetheless cancel a training session, or tell a workout buddy they are not going to the fitness center today). Moreover, these approaches require a fitness center to accommodate all of the possible forms of interaction with the member of the fitness center (e.g., a member may need to call the fitness center to schedule a training session, go to the fitness center in person to get a spot in a class, and the like). From a member's perspective, the lack of centralization of interactions with the fitness center can require more effort from the member than he is willing to expend, and perhaps even dissuade the member from going to the fitness center. Not only may this adversely affect the member (e.g., the member may lose motivation and may not meet their workout goals), but this may also adversely affect the fitness provider as an un-motivated member may be more likely to cancel their membership (e.g., thus causing the fitness center to lose income).

SUMMARY OF THE DISCLOSURE

This is directed to systems and methods for accessing personalized fitness services using a portable electronic devices.

An electronic device may include a single, seamless application to introduce new customers to a fitness center and motivate these new customers to keep returning to the fitness center as active members. In some embodiments, the integrated application can be provided on a portable electronic device such as a cellular phone, a laptop, a portable media player, or other suitable electronic device.

To interface with a fitness center, the integrated application can, for example, securely connect to one or more servers associated with the fitness center. For example, the integrated application can connect with distinct servers associated with scheduling training sessions, accessing gym equipment guides, mapping directions to the fitness center, paying membership fees, communicated with exercise equipment of the fitness center, or any other suitable servers.

In some embodiments, the integrated application can provide functions to introduce potential new customers to a fitness center. For example, the integrated application can showcase available classes and service of the fitness provider, provide fitness center locators, provide free passes to the fitness center, provide other promotions, provide affiliate offers, and any combination of the above.

In some embodiments, the integrated application can provide functions to motivate a customer to join the fitness center (e.g., after the customer has been introduced to the fitness center) and actively attend the fitness center. For example, the integrated application can provide the user with news and updates associated with the fitness center, can provide daily promotions, can provide a scheduler (e.g., to allow a user to schedule session with a fitness trainer, to schedule classes, and the like), can provide social networking features (e.g., to help a user find a workout buddy, and any combination of the above).

In some embodiments, the integrated application can provide in-gym motivation. For example, the integrated application can allow a user to access equipment guides, can allow a user to access workout videos, can track a user's workout routine in real-time (e.g., display on a screen of a portable electronic device the treadmill's speed, the amount of weight being used on a piece of exercise equipment, and the like), can promote competition among members of the fitness center (e.g., thus motivating fitness center members to "beat one another's scores" and workout harder), and any combination of the above.

In some embodiments, the integrated application can provide post-workout motivation. For example, the integrated application can provide a user with coupons that may help a user re-energize (e.g., power drink coupons, spa coupons, and the like), can provide reminders prompting a user to return to the fitness center, can provide up-sell opportunities (e.g., by selling a music playlist from a class the user took), can provide analytical tools for analyzing a user's past workout information, and any combination of the above.

BRIEF DESCRIPTION OF THE DRAWINGS

The above and other features of the invention, its nature and various advantages will be more apparent upon consideration of the following detailed description, taken in conjunction with the accompanying drawings in which.

DETAILED DESCRIPTION

Figure 1:
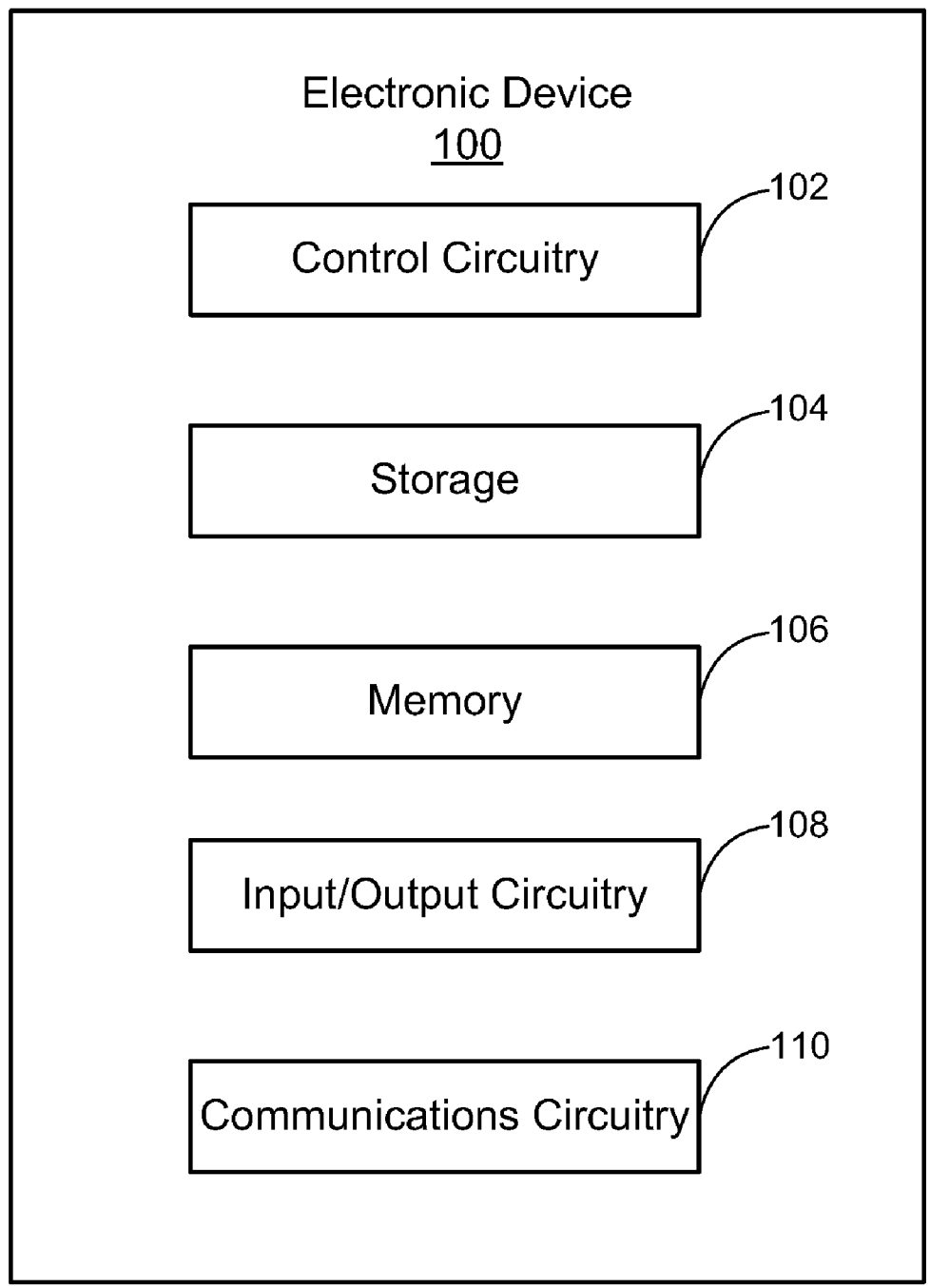
FIG. 1 is a schematic view of an illustrative electronic device for providing an integrated application operative to interface with a fitness center in accordance with some embodiments of the invention.

FIG. 1 is a schematic view of an illustrative electronic device for providing an application operative to interface with a fitness center in accordance with some embodiments of the invention. Electronic device 100 can include control circuitry 102, storage 104, memory 106, input/output ("I/O") circuitry 108, and communications circuitry 110. In some embodiments, one or more of the components of electronic device 100 can be combined or omitted (e.g., storage 104 and memory 106 may be combined). In some embodiments, electronic device 100 can include other components not combined or included in those shown in FIG. 1 (e.g., motion detection components, a power supply such as a battery or kinetics, a display, bus, a positioning system, a camera, an input mechanism, etc.), or several instances of the components shown in FIG. 1. For the sake of simplicity, only one of each of the components is shown in FIG. 1.

Electronic device 100 can include any suitable type of electronic device. For example, electronic device 100 can include a portable electronic device that the user may hold in his or her hand, such as a digital media player (e.g., an iPod™ made available by Apple Inc. of Cupertino, Calif.), a personal e-mail device (e.g., a Blackberry™ made available by Research in Motion of Waterloo, Ontario), a personal data assistant ("PDA"), a cellular telephone, a handheld gaming device, and a digital camera. As another example, electronic device 100 can include a larger portable electronic device, such as a laptop computer. As yet another example, electronic device 100 can include a substantially fixed electronic device, such as a desktop computer.

Control circuitry 102 can include any processing circuitry or processor operative to control the operations and performance of electronic device 100. For example, control circuitry 102 can be used to run operating system applications, firmware applications, media playback applications, media editing applications, or any other application. In some embodiments, control circuitry 102 can drive a display and process inputs received from a user interface.

Storage 104 can include, for example, one or more storage mediums including a hard-drive, solid state drive, flash memory, permanent memory such as ROM, any other suitable type of storage component, or any combination thereof. Storage 104 can store, for example, media data (e.g., music and video files), application data (e.g., for implementing functions on electronic device 100), firmware, user preference information data (e.g., media playback preferences), authentication information (e.g. libraries of data associated with authorized users), lifestyle information data (e.g., food preferences), exercise information data (e.g., information obtained by exercise monitoring equipment), transaction information data (e.g., information such as credit card information), wireless connection information data (e.g., information that can enable electronic device 100 to establish a wireless connection), subscription information data (e.g., information that keeps track of podcasts or television shows or other media a user subscribes to), contact information data (e.g., telephone numbers and email addresses), calendar information data, and any other suitable data or any combination thereof.

Memory 106 can include cache memory, semi-permanent memory such as RAM, and/or one or more different types of memory used for temporarily storing data. In some embodiments, memory 106 can also be used for storing data used to operate electronic device applications, or any other type of data that can be stored in storage 104. In some embodiments, memory 106 and storage 104 can be combined as a single storage medium.

I/O circuitry 108 can be operative to convert (and encode/decode, if necessary) analog signals and other signals into digital data. In some embodiments, I/O circuitry 108 can also convert digital data into any other type of signal, and vice-versa. For example, I/O circuitry 108 can receive and convert physical contact inputs (e.g., from a multi-touch screen), physical movements (e.g., from a mouse or sensor), analog audio signals (e.g., from a microphone), or any other input. The digital data can be provided to and received from control circuitry 102, storage 104, memory 106, or any other component of electronic device 100. Although I/O circuitry 108 is illustrated in FIG. 1 as a single component of electronic device 100, several instances of I/O circuitry 108 can be included in electronic device 100.

Electronic device 100 can include any suitable interface or component for allowing a user to provide inputs to I/O circuitry 108. For example, electronic device 100 can include any suitable input mechanism, such as for example, a button, keypad, dial, a click wheel, or a touch screen. In some embodiments, electronic device 100 can include a capacitive sensing mechanism, or a multi-touch capacitive sensing mechanism.

In some embodiments, electronic device 100 can include specialized output circuitry associated with output devices such as, for example, one or more audio outputs. The audio output can include one or more speakers (e.g., mono or stereo speakers) built into electronic device 100, or an audio component that is remotely coupled to electronic device 100 (e.g., a headset, headphones or earbuds that can be coupled to communications device with a wire or wirelessly).

In some embodiments, I/O circuitry 108 can include display circuitry (e.g., a screen or projection system) for providing a display visible to the user. For example, the display circuitry can include a screen (e.g., an LCD screen) that is incorporated in electronics device 100. As another example, the display circuitry can include a movable display or a projecting system for providing a display of content on a surface remote from electronic device 100 (e.g., a video projector). In some embodiments, the display circuitry can include a coder/decoder (Codec) to convert digital media data into analog signals. For example, the display circuitry (or other appropriate circuitry within electronic device 100) can include video CODECs, audio CODECs, or any other suitable type of Codec.

The display circuitry also can include display driver circuitry, circuitry for driving display drivers, or both. The display circuitry can be operative to display content (e.g., media playback information, application screens for applications implemented on the electronic device, information regarding ongoing communications operations, information regarding incoming communications requests, or device operation screens) under the direction of control circuitry 102. Alternatively, the display circuitry can be operative to provide instructions to a remote display.

Communications circuitry 110 can include any suitable communications circuitry operative to connect to a communications network and to transmit communications (e.g., voice or data) from electronic device 100 to other devices within the communications network. Communications circuitry 110 can be operative to interface with the communications network using any suitable communications protocol such as, for example, Wi-Fi (e.g., a 802.11 protocol), Bluetooth®, radio frequency systems (e.g., 900 MHz, 1.4 GHz, and 5.6 GHz communication systems), infrared, GSM, GSM plus EDGE, CDMA, quadband, and other cellular protocols, VOIP, or any other suitable protocol.

In some embodiments, communications circuitry 110 can be operative to create a communications network using any suitable communications protocol. For example, communications circuitry 110 can create a short-range communications network using a short-range communications protocol to connect to other devices. For example, communications circuitry 110 can be operative to create a local communications network using the Bluetooth® protocol to couple electronic device 100 with a Bluetooth® headset.

Electronic device 100 can include one more instances of communications circuitry 110 for simultaneously performing several communications operations using different communications networks, although only one is shown in FIG. 1 to avoid overcomplicating the drawing. For example, electronic device 100 can include a first instance of communications circuitry 110 for communicating over a cellular network, and a second instance of communications circuitry 110 for communicating over Wi-Fi or using Bluetooth®. In some embodiments, the same instance of communications circuitry 110 can be operative to provide for communications over several communications networks.

In some embodiments, electronic device 100 can be coupled a host device for data transfers, synching the communications device, software or firmware updates, providing performance information to a remote source, or performing any other suitable operation that can require electronic device 100 to be coupled to a host device. Several electronic devices 100 can be coupled to a single host device using the host device as a server. Alternatively or additionally, electronic device 100 can be coupled to several host devices (e.g., for each of the plurality of the host devices to serve as a backup for data stored in electronic device 100).

In some embodiments, an electronic device (e.g., electronic device 100 of FIG. 1) may include a single, integrated application operative to interface with a fitness center to provide access to different services associated with the fitness center. These services can span the full range of a fitness center experience and can include everything from engaging and introducing a user to a new fitness center to motivating the user to actively return to the fitness center on a regular basis. In this manner, through an integrated application, a fitness center can maintain a constant connection between themselves and the user. This can result in personalizing a user's fitness center experience, and can help a user to get started at a particular fitness center and then continue actively working out at this fitness center.

Figure 2:
FIGS. 2-3 are schematic views of several situations during which a user can make use of a single, integrated application in the context of a fitness center experience in accordance with some embodiments of the invention.

Moreover, the integrated application can further enhance a user's fitness center experience by addressing the needs and questions encountered by a user during their fitness center experience. For example, FIG. 2 shows schematic view 200 of illustrative questions and needs of a user that the integrated application can address. For example, the integrated application can aid a user in locating a fitness center, can aid a user in finding information on and scheduling personal trainer sessions, can provide information related to fitness center classes, can provide workout analysis information such as how many calories were burned in a particular workout, can provide social networking features to help a user find workout buddies, can help a user identify if and how they are improving, can provide equipment guides, and can provide competitive and score-keeping functions such as a leaderboard.

To interface with the fitness center, the integrated application can use any suitable approach. In some embodiments, the electronic device can securely connect to one or more servers associated with the fitness center (e.g., through communication circuitry 110 of FIG. 1). For example, the integrated application can connect with a calendar server of the fitness center to schedule a session with a fitness trainer, to reserve a spot in a fitness center class, or perform other scheduling functions. As another example, the integrated application can connect to a mapping application to provide directions to the fitness center, generate a map to the fitness center, and the like. As another example, the integrated application can connect to a secure server to allow the user to enter payment information (e.g., credit card information) to, for example, pay fitness center membership fees, pay for sessions with a fitness trainer, purchase food and drinks (e.g., a power bar, water, or other consumables offered for sale in a store of the fitness center), purchase workout attire for sale in a store of the fitness center, or pay for any other suitable items.

Figure 3:
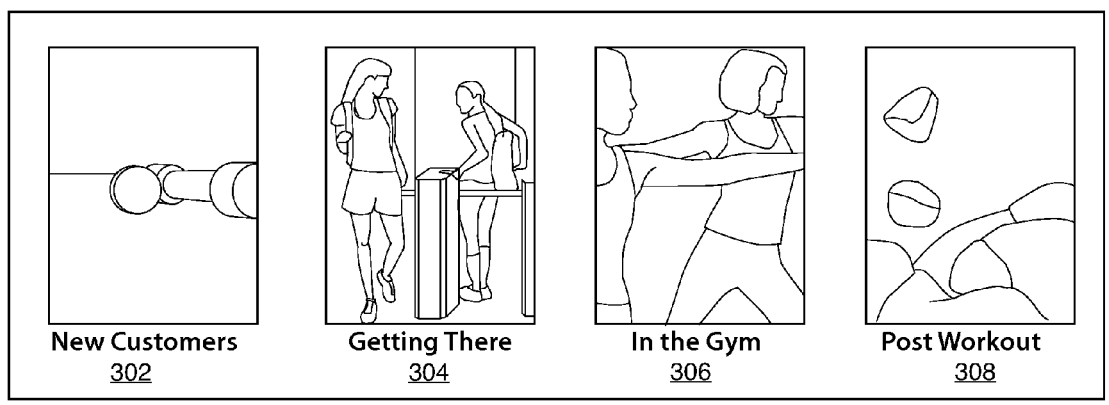

Accordingly, through an integrated application of an electronic device, a user can perform different operations to enhance the user's fitness center experience and become motivated to actively return to the fitness center. FIG. 3 shows diagram 300 of several situations during which a user can make use of a single, integrated application in the context of a fitness center experience.

As shown in diagram 300, the integrated application could be used in new customer scenario 302. For example, the integrated application can help potential new customers to locate a fitness center, become educated about the fitness center, and can generate user interest in this fitness center. The integrated application can moreover be used in getting there scenario 304. For example, the integrated application can motivate users to join the fitness center and then actively or regularly visit the fitness center to workout. As shown in diagram, another scenario can include in-gym scenario 306 when the user is working out at the fitness center. For example, the integrated application can enrich a user's fitness center experience by providing in-gym functionality and motivation. The integrated application can furthermore be used in post-workout scenario 308 after the user has completed a workout at the fitness center. For example, the integrated application can provide functions and services to help a user to re-charge after working out, and motivate the user to return to the fitness center again.

Figure 4:
FIG. 4 is a schematic view of functions available for introducing a potential new customer to a fitness center in accordance with some embodiments of the invention.

FIG. 4 shows diagram 400 of illustrative functions related to attracting and engaging new customers through a single, integrated application. For example, the functions of FIG. 4 may be available to a user during new customer scenario 302 of FIG. 3. However, one skilled in the art could appreciate that the functions of FIG. 4 are not limited to a new customer scenario or to the particular functions listed in FIG. 4, and rather may include any suitable functions or be used in any suitable scenario.

As shown in FIG. 4, the integrated application can introduce a user to a particular fitness center by showcasing available classes or other services provided by the fitness center. For example, the integrated application can access a server of the fitness center to receive information associated with the available classes and services. The integrated application may then generate and display a menu or other suitable interface on the user's electronic device showing this information. For example, interface 402 shows an exemplary interface for displaying information associated with available services on electronic device 404. Interface 402 is a rendition of a webpage interface used in a website originally provided by 24 Hour Fitness, headquartered in San Ramon, Calif. This interface is a third-party product provided as an example of many interfaces that could be used to display fitness center services as discussed herein. The information associated with the available services can include, for example, class names, class descriptions, a class schedule, description of equipment available in the fitness center, description of locker rooms, description of a pool in the fitness center, description of rock climbing facilities, description of personal fitness trainer services, fitness center hours of operation, any other suitable services information, or any combination of the above. In this manner, a user can be provided with a convenient and easy way of acquiring information related to the fitness center.

As is also shown in FIG. 4, the integrated application can provide a fitness center locator. For example, a mapping application can be accessed to determine the location or locations of the fitness center. A map of the local area nearby the fitness center, directions and a map to the fitness center, or other suitable mapping functions may be generated by the integrated application and accessed by the user. For example, the maps can be displayed on a display screen of the user's electronic device.

In some embodiments, free passes, membership promotions, affiliate offers, or other suitable offers can be provided to a user through the integrated application. The offers may, for example, help to generate user interest in the fitness center and encourage a user to initially visit the fitness center (e.g., thus increasing the possibility that the user will join the fitness center). For example, free passes such as free pass 406 can be provided directly to a user's electronic device 408 through the integrated application. A user may redeem the free pass by, for example, showing free pass 406 to a worker at the fitness center, choosing a suitable input such as input 410, or through any other suitable method. Additionally or alternatively, membership promotions can be provided to encourage a user to join the fitness center. For example, a membership promotion such as, "Join our fitness center within 10 days and receive a 20% discount for the year" can be provided directly to a user through the integrated application. As another example, affiliate offers such as workout attire, exercise equipment, power drinks, power bars, and other suitable items available for purchase from an affiliate company can be provided directly to a user through the integrated application. The free passes, membership promotions, affiliate offers, or other offers can include any suitable notification such as, for example, an e-mail, a text message, a voicemail, a pop-up message, a push notification (e.g., a notification that utilizes an internet protocol ("IP") connection to forward notifications from the servers of third party applications to an electronic device), any other suitable notification, or any combination of the above.

Figure 5:
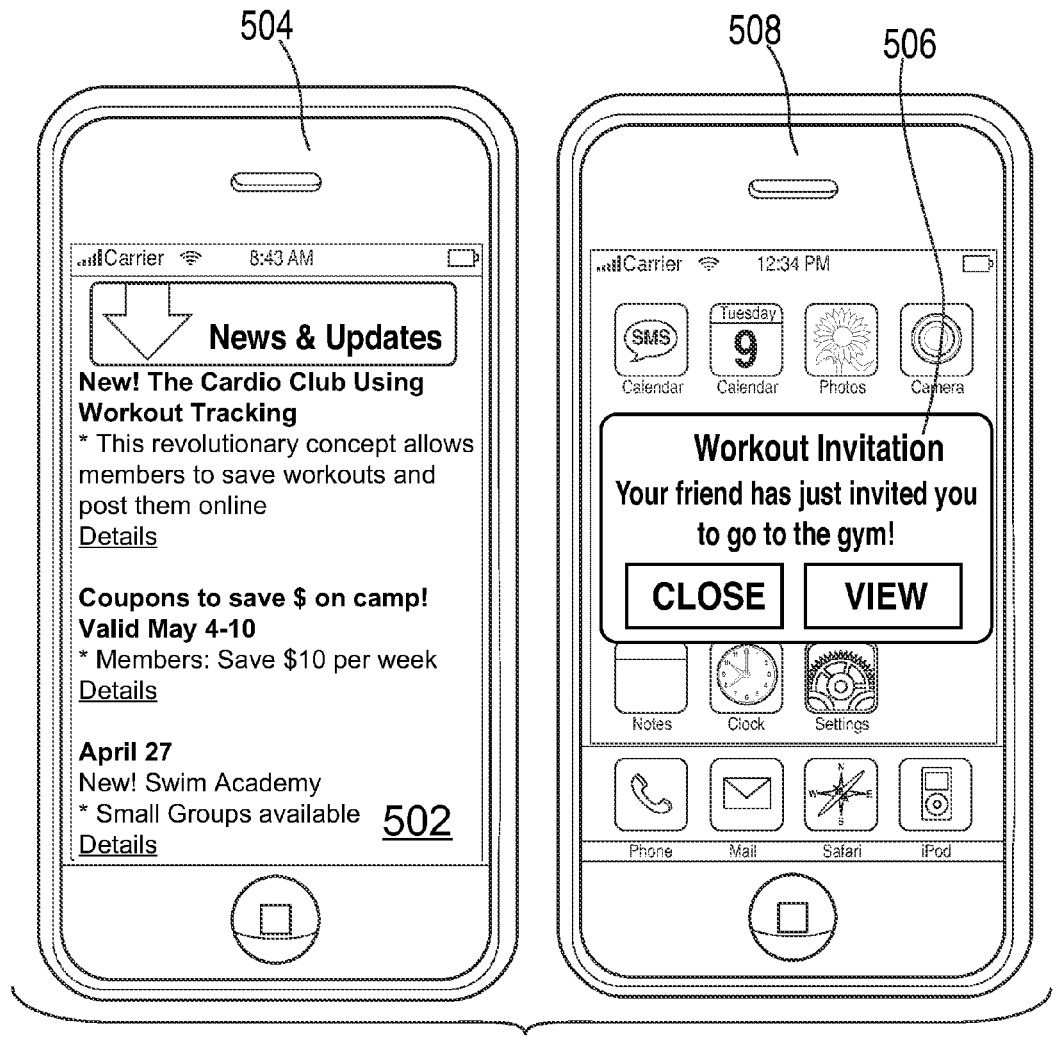
FIG. 5 is a schematic view of functions available for motivating a customer to join and actively attend a fitness center in accordance with some embodiments of the invention.

In this manner, as illustrated by diagram 400, a user can be introduced to and educated about a particular fitness center through an integrated application of their electronic device. Once this "conversation" has been opened with a user, a user can be motivated to join and actively visit the fitness center through this integrated application. For example, FIG. 5 shows diagram 500 of illustrative functions that a customer can access through an integrated application, where these functions may motivate the customer to join and actively visit a fitness center. For example, the functions of FIG. 5 may be available to a user during getting there scenario 304 of FIG. 3. However, one skilled in the art could appreciate that the functions of FIG. 5 are not limited to a getting there scenario or to the particular functions listed in FIG. 5, and rather may include any suitable functions or be used in any suitable scenario.

As shown in diagram 500, news and updates associated with a fitness center can be provided to a user through the integrated application. For example, interface 502 shows an exemplary interface for providing news and updates to a user through electronic device 504. Interface 502 is a rendition of a webpage interface used in a website originally provided by the Young Men's Christian Association (the "YMCA") headquartered in Chicago, Ill. This interface is a third-party product provided as an example of many interfaces that could be used to display news and updates as discussed herein. By providing the news and updates conveniently and directly to a user in this manner, the user may become excited and interested in the available resources of the fitness center, and thus may be encouraged to join and actively visit the fitness center. Moreover, in some embodiments, daily promotions and activities can be provided to a user. For example, promotions and activities such as "%10 discount on all power shakes today!" or "free rock climbing lessons available from 1-5 PM this afternoon" and the like can be provided directly to a user.

As is also shown in diagram 500, a scheduler can be provided through the integrated application. For example, the integrated application can access an integrated or accessible calendar application, thus allowing the integrated application to identify a user's daily schedule. The integrated application may schedule visits to the fitness center into the user's calendar. For example, the integrated application can schedule general workouts (e.g., "go to the gym on September 5 after work at 7 PM"), specific workouts (e.g., "do 1 hour of treadmill work and 1 hour of upper body weight lifting on September 12 at 1 PM"), or any combination of the above. In some embodiments, the integrated application can automatically determine a suitable workout schedule and log this schedule into the user's calendar. The suitable workout schedule may, for example, be personalized for the user based on the user's age, gender, strength, previous workout statistics, any other suitable factors, or any combination of the above (e.g., a harder workout can be scheduled for a user in their 20's, an easier workout can be scheduled for a user in their 60's, and the like). Alternatively or additionally, a user may manually determine a workout schedule.

In some embodiments, the integrated application can provide reminders to visit the fitness center. For example, the integrated application can provide a reminder of a scheduled workout to the user through an e-mail message, a pop-up notification, a push notification, an alarm, a text message, a voice mail, or through any other suitable notification. As another example, the integrated application can provide reminders of the amount of time that has passed since a user last visited the fitness center.

As is also indicated by diagram 500, the integrated application can provide social networking features to, for example, aid a user in finding a workout buddy (e.g., where a workout buddy and user may encourage each other to visit the fitness center on a regular basis). For example, in some embodiments, a user can send a request for a workout buddy or other requests to members of a social network. In some embodiments, the integrated application can match the user with potential workout buddies through user preferences. User preferences can determine any suitable attributes of the user such as, for example, age, gender, athletic abilities, preferred exercises, preferred workout times, fitness center at which the user is a member, preferred workout locations, any other suitable attributes, or any combination of the above. The user's preferences may then be compared to preferences of members of the social network to determine which members may be a suitable match for the user. The integrated application may then provide a notice of the matching members to the user, or otherwise introduce the user to the matching members.

In this manner, through the social networking features provided by the integrated application, a user can meet and communicate with workout buddies, thereby potentially provide encouragement for the user to visit the fitness center. For example, through the social networking features, members of the social network may schedule workouts together, invite one another to go to the fitness center, exchange advice and feedback regarding the fitness center, workouts, exercise equipment, or other aspects of the fitness center, or otherwise communicate with one another regarding fitness topics. For example, notification 506 shows an exemplary social networking notification that can be provided to a user through electronic device 508. As an illustration, a workout buddy or other member of the social network may invite the user to go to the fitness center or provide any other suitable communication to the user through notification 506.

Figure 6:
FIG. 6 is a schematic view of functions available to provide in-gym motivation in accordance with some embodiments of the invention.

FIG. 6 shows diagram 600 of illustrative functions related to providing in-gym motivation through the integrated application. By providing workout motivation to a user while they are in the fitness center, a user's workout experience may be enriched and enhanced, and the user can be motivated to return to the fitness center on an active basis. The functions of FIG. 6 may be available to a user, for example, during in-gym scenario 306 of FIG. 3. However, one skilled in the art could appreciate that the functions of FIG. 6 are not limited to an in-gym scenario or to the particular functions listed in FIG. 6, and rather may include any suitable functions or be used in any suitable scenario.

As indicated in diagram 600, up-sell opportunities such as advertisements for sessions with a personal trainer, advertisements for items available for purchase from a store of the fitness center (e.g., food, drinks, athletic wear, or any other suitable items), advertisements for classes, or any other suitable up-sell opportunities can be provided to a user through the integrated application. For example, interface 602 shows an exemplary interface for providing up-sell opportunities directly to a user through their electronic device. Interface 602 is a rendition of a webpage interface used in a website originally provided by the Equinox Fitness headquartered in New York, N.Y. This interface is a third-party product provided as an example of many interfaces that could be used to display purchasable items as discussed herein.

In some embodiments, in-gym motivation can be encouraged by providing workout programs, workout videos, and how-to guides for exercise equipment through the integrated application. For example, a workout program or video can be received through the integrated application and played back on the user's electronic device at the user's convenience. In this manner, a user may have access to a "personal teacher" who can guide the user through a particular workout program (e.g., a cardio workout, a spinning class, or any other suitable workout program) whenever the user is at the fitness center or whenever the user desires. This may remove the need for a user to adjust their personal schedule or otherwise plan their day around a class at a fitness center, and may alternatively allow the user to enjoy a workout class at their own convenience.

Similarly, in some embodiments the integrated application can operate as a "personal trainer" by providing how-to guides for exercise equipment of the fitness center. For example, oftentimes a user may be uncertain how to operate a piece of exercise equipment or may be unsure of how much weight to place on it, thus potentially discouraging the user from working out with that piece of equipment. Accordingly, the integrated application can provide how-to guides which may instruct a user on how to use a particular piece of equipment, instruct the user on which exercise to perform on the piece of equipment, instruct the user on how much weight to use, instruct the user on how many repetitions to perform, or otherwise operate as a personal trainer for the user.

In some embodiments, the exercise equipment can be physically or wirelessly coupled to a user's electronic device. For example, the exercise equipment can include a port or other connector operative to physically couple a user's electronic device to the exercise equipment. As another example, a Bluetooth® connection, WiFi connection, or other suitable wireless connection can be used to wirelessly couple the exercise equipment to a user's electronic device (e.g., via communications circuitry 110 of FIG. 1). This coupling may allow the integrated application of the electronic device to communicate with the exercise equipment to, for example, instruct the exercise equipment to automatically adjust the amount of weight, adjust the seating and height settings of the exercise equipment, or adjust any other suitable setting of the exercise equipment. For example, the integrated application can have access to user attributes defining the user such as height, weight, athletic abilities, prior workout history, or any other suitable attributes. Based on these user attributes, the integrated can instruct the exercise equipment to adjust its settings accordingly (e.g., the integrated application can instruct the exercise equipment to adjust its seat settings based on the height of the user, can instruct the exercise equipment to adjust the amount of weight used based on the user's prior workout history, and the like).

As is also shown in diagram 500, a user's workout experience can be enriched by providing workout tracking to actively inform a user of their workout performance. For example, the integrated application can communicate with exercise equipment to determine information such as current speed (e.g., treadmill speed, elliptical speed, or other equipment speed), current weight on the exercise equipment, current number of repetitions, or other suitable information, and then may provide this information to the user. For example, this information can be displayed on a display screen of the user's electronic device in real-time. As another example, the electronic device can include sensors operable to measure physiological data of the user such as heart rate, breathing speed, or other suitable data. This information may similarly be provided to the user by, for example, displaying the physiological data on a display screen of the user's electronic device. In some embodiments, the determined information can be stored for later use by the user (e.g., for viewing past workout history, for monitoring performance or improvement, or for any other suitable use). The determined information can be stored in the user's electronic device (e.g., stored in storage 104 of FIG. 1), stored in a remote database that is in communication with the integrated application, or stored in any other suitable storage device.

In some embodiments, social networking functions, competitions, leaderboards, and the like can be provided through the integrated application to promote competition among the members of the fitness center. This competition may, for example, motivate users to workout harder, visit the fitness center more often, or otherwise actively visit the fitness center to improve their abilities and beat one another's workout accomplishments. For example, in some embodiments, accomplishments of a user can be transmitted to members of the social network. For example, notification 604 shows an exemplary notification that can be transmitted to electronic device 606 of a member of the social network. Notification 604 may, for example, advertise that a member of the social network has just accomplished a certain achievement (e.g., "Amanda just ran 1 mile in 6:34 minutes!"). Moreover, notification 604 can promote competition or otherwise encourage other members of the social network to workout and visit the fitness center (e.g., by challenging a user to "beat that" achievement of the other member of the social network). A user may, for example, except the challenge or otherwise reply to notification 604 through a suitable input such as input 608. Notification 604 can include any suitable notification such as, for example, an e-mail, a text message, a voicemail, a pop-up message, a push notification (e.g., a notification that utilizes an internet protocol ("IP") connection to forward notifications from the servers of third party applications to an electronic device), any other suitable notification, or any combination of the above.

In this manner, through the social networking and competition-building features of the integrated application, the members of the fitness center can be provided with a real-time, connected experience. For example, upon a user completing a certain achievement, the members of the fitness center can be immediately informed of the user's achievement (e.g., the members can receive a notification reading "Bob just bench pressed 300 pounds!" immediately after this achievement is accomplished). Moreover, this can allow the members of the fitness center to boast of their accomplishments and challenge one another to beat their achievements. This may build competition among the members of the gym, and actively encourage the members to visit the fitness center and workout.

Figure 7:
FIG. 7 is a schematic view of functions available to provide post-workout motivation in accordance with some embodiments of the invention.

FIG. 7 shows diagram 700 of illustrative functions related to providing post-workout motivation through the integrated application. The functions of FIG. 7 may be available to a user, for example, during post-workout scenario 308 of FIG. 3, and may be used to re-charge a user after completing a workout and re-motivate them to return to the fitness center again. However, one skilled in the art could appreciate that the functions of FIG. 7 are not limited to a post-workout scenario or to the particular functions listed in FIG. 7, and rather may include any suitable functions or be used in any suitable scenario.

As shown in diagram 700, after a workout has been completed, a user can be provided with coupons, promotions, and affiliate offers that may re-energize or otherwise motivate the user to return to the fitness center. For example, promotions such as coupons for a sports drink, coupons for a spa appointment, coupons for a power bar, or any other suitable promotions can be provided through the integrated application. For example, promotion 702 shows an illustrative coupon that can be provided to a user through electronic device 704. As illustrated by promotion 702, in some embodiments the coupon can be provided to the user in response to completing a particular workout goal (e.g., in order to reward the user). To redeem promotion 702, the user may, for example, show promotion 702 to the provider of the coupon item, choosing a suitable input such as input 706, or use any other suitable way.

As is also shown in diagram 700, the integrated application can provide a scheduler and reminders to a user. For example, the integrated application can determine when a user last visited a fitness center by, for example, accessing a calendar application of the user, determining when the electronic device was last coupled to a piece of exercise equipment at the fitness center, identifying an invitation from a workout buddy to go to the fitness center that was accepted by the user, or through any other suitable way. The integrated application may determine the amount of time that has passed since this last visit, and provide a suitable reminder to the user. For example, notification 708 shows an illustrative notification that can be provided to electronic device 710 to remind a user of their last visit to the fitness center. In some embodiments, suitable options associated with returning to the fitness center can be provided through notification 708, such as option 712 to book a session with a fitness trainer, option 714 to add a workout session to the user's calendar, or any other suitable option. In this manner, a user can be encouraged or provided with additional motivation for returning to the fitness center.

Through the integrated application, up-sell opportunities associated with a post-workout scenario can be provided to the user. For example, during a workout, a user may attend a class (e.g., a spinning class, a cardio class, a Pilates class, or any other suitable fitness center class) that played a music playlist during the class. This music playlist may then be offered for sale to the user through the integrated application. For example, a notification offering to sell the music playlist can be sent to an electronic device of the user. As another example, a user can access an interface of the fitness center through which purchases of music playlists of classes which the user has attended can be purchased. This can be beneficial for a user when, for example, the user attended a certain class in which they found its music playlist to be especially motivating or agreeable. Through the integrated application, the user may then be provided with a convenient and easy way of locating and accessing this motivating music playlist.

As is also shown in diagram 700, analytical tools such as charts and diagrams can be provided to the user through the integrated application. For example, the integrated application can communicate with one or more pieces of exercise equipment to determine a user's past workout information. The past workout information can include, for example, equipment use data (e.g., speed on a treadmill, speed on an elliptical, amount of weights used on a piece of exercise equipment, number of repetitions performed on a piece of exercise equipment, amount of time for which the piece of equipment was used, distance traveled, and the like), date on which the piece of equipment was used, time at which the piece of equipment was used, or any other suitable past workout information. As another example, the integrated application can communicate with a physiological sensor to determine past workout information such as the user's heart rate (e.g., while using a certain piece of exercise equipment), the user's breathing speed, or other suitable physiological data. As another example, the user may manually enter past workout information such as equipment use data, dietary information (e.g., what foods the user ate before working out on a certain date), clothing information (e.g., whether the user wore notable sports clothing, such as a particular type of running sneaker, while using a piece of exercise equipment on a certain date), or any other suitable information. Although certain ways of determining past workout information are described above, one skilled in the art could appreciate that an integrated application could alternatively or additionally determine past work out information in any suitable manner.

Based on the past workout information, the integrated application can generate analytical tools to aid a user in an analysis their workout history. For example, the integrated application may generate charts, graphs, or any other suitable diagrams showing information such as performance data versus time on a piece of exercise equipment (e.g., speed versus time, amount of weight versus time, incline of a treadmill versus time, or any other suitable performance data), physiological data versus time (e.g., breathing rate versus time, heart rate versus time, and the like), which exercise equipment was used on which days, how many repetitions were performed on a piece of exercise equipment on which days, what the user ate on which days, how many calories were consumed on which days, how many calories the user burned on which days, what distance the user traveled on which days, which exercise classes were attended on which days, or any other suitable information. These generated diagrams may be, for example, accessible through a menu or other interface displayed on a display screen of the user's electronic device. In this manner, with these diagrams, the user can be presented with a convenient and visual representation of their workout history. This may beneficially allow the user to identify areas or exercise requiring improvement, areas of exercise that are meeting workout goals, or other workout trends and can result in keeping a user interested in working out and motivated to visit the fitness center.

Figure 8:
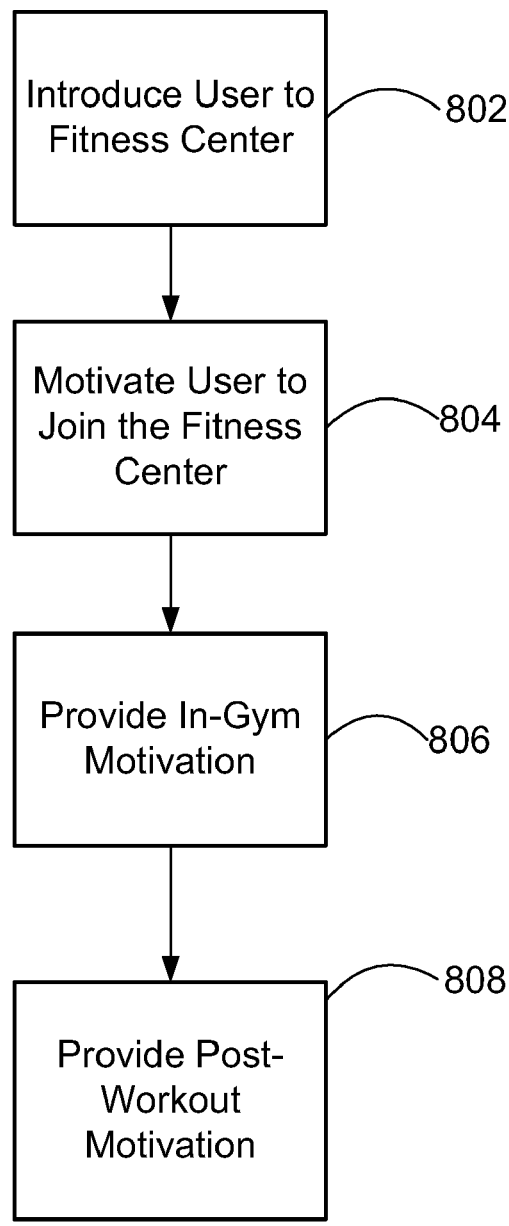
FIG. 8 is an illustrative process for interfacing with a fitness center in accordance with some embodiments of the invention.

As described above, the functions available through the integrated application can introduce a new user to a fitness center and can provide motivation for the user to workout actively. In this manner, not only may a user be motivated to actively return to a fitness center, but the fitness center may be provided with a frequent and loyal customer. FIG. 8 shows illustrative process 800 for interfacing with a fitness center to provide workout motivation to a user in accordance with some embodiments of the invention.

At step 802, a user (e.g., a potential new customer) can be introduced to a fitness center. For example, a menu or other suitable interface can be provided on an electronic device of the user to showcase available classes and service of the fitness provider. As another example, a fitness center locator can be accessed through the electronic device to aid a user in locating and traveling to the fitness center. As yet another example, offers such as free passes to the fitness center, membership offers, promotions, and affiliate offers can be transmitted to the electronic device.

At step 804, the user can be motivated to join the fitness center and actively attend the fitness center. For example, news and updates associated with the fitness center and daily promotions can be transmitted to the electronic device. As another example, the electronic device may interface with the fitness center to provide scheduling functions such as, for example, scheduling a session with a personal fitness trainer, reserving a spot in a fitness center class, and the like. As yet another example, the electronic device can communicate with a social network of the fitness center to provide social networking features (e.g., to help a user find a workout buddy).

At step 806, the user can be provided with in-gym motivation. For example, the electronic device can communicate with the fitness center to access equipment guides and workout videos for playback to the user. As another example, the electronic device can communicate with one or more pieces of workout equipment of the fitness center to track the user's workout routine in real-time (e.g., display a treadmill's speed on a display screen of the electronic device, display the amount of weight being used on a piece of exercise equipment on a display screen of the electronic device, and the like). As another example, the electronic device can interface with a social network of the fitness center to share workout achievements and other information with the members of the social network. This may, for example, promote competition among members of the fitness center and motivate them to workout harder to better one another's workout achievements.

At step 808, the user can be provided with post-workout motivation. For example, coupons that may help a user to re-energize and re-motivate (e.g., power drink coupons, spa coupons, power bar coupons, and the like), reminders prompting a user to return to the fitness center, and up-sell opportunities (e.g., selling a music playlist from a class which the user took) can be transmitted to the electronic device. As another example, analytical charts, graphs, or other suitable diagrams associated with a user's past workout information can be provided through the electronic device directly to the user.

The process discussed above is intended to be illustrative and not limiting. Persons skilled in the art could appreciate that steps of the process discussed herein can be omitted, modified, combined, or rearranged, and any additional steps can be performed without departing from the scope of the invention.

The inventions can be implemented by software, but can also be implemented in hardware or a combination of hardware and software. The invention can also be embodied as computer-readable code on a computer-readable medium. The computer-readable medium can include any data storage device that can store data which can thereafter be read by a computer system. Examples of the computer readable medium include read-only memory ("ROM"), random-access memory ("RAM"), CD-ROMs, DVDs, magnetic tape, optical data storage device, flash storage devices, or any other suitable storage devices. The computer-readable medium can also be distributed over network coupled computer systems so that the computer readable code is stored and executed in a distributed fashion.

Insubstantial changes from the claimed subject matter as viewed by a person with ordinary skill in the art, now known or later devised, are expressly contemplated as being equivalently within the scope of this disclosure. Therefore, obvious substitutions now or later known to one with ordinary skill in the art are defined to be within the scope of the defined elements.

The above-described embodiments of the present invention are presented for purposes of illustration and not of limitation.

What is claimed is:

1. A method for interfacing with a fitness center, the method comprising:
    introducing a user to a particular fitness center via an integrated application of a portable electronic device, wherein the user is a potential new customer of the particular fitness center;
    after the introducing, providing incentive, via the integrated application, for the user to join the particular fitness center;
    in response to the user joining the particular fitness center as a result of the incentive, providing, via the integrated application, in-gym motivation for motivating the user to work out at the particular fitness center; and
    providing, via the integrated application, post-workout motivation to encourage the user to actively return to the particular fitness center, wherein at least one of the providing incentive, the providing in-gym motivation, and the providing post-workout motivation comprises connecting the user, via the integrated application, with a calendar server of the particular fitness center for allowing the user to perform a scheduling function with the particular fitness center.

2. The method of claim 1, wherein introducing comprises:
    transmitting a free pass to visit the particular fitness center to the portable electronic device.

3. The method of claim 1, wherein introducing comprises:
    transmitting at least one of a membership promotion and an affiliate offer associated with the particular fitness Center to the portable electronic device.

4. The method of claim 1, wherein providing incentive, via the integrated application, for the user to join the particular fitness center comprises:
    transmitting at least one of news, updates, daily promotions, and daily activities associated with the particular fitness center to the portable electronic device.

5. The method of claim 1, wherein providing incentive, via the integrated application, for the user to join the particular fitness center comprises:
    identifying at least one member of a social network of the particular fitness center for recommending as a workout buddy to the user; and providing a recommendation of the at least one member to the user through the integrated application.

6. The method of claim 5, wherein identifying comprises:
receiving at least one user preference associated with the user;
comparing the at least one user preference associated with the user to user preferences associated with members of the social network; and
determining the at least one user preferences matches a user preference of the one member.

7. The method of claim 6, wherein the at least one user preference associated with the user comprises at least one of age, gender, athletic ability, a preferred exercise type, a preferred workout time, a fitness center at which the user is a member, and a preferred workout location.

8. The method of claim 1, wherein providing, via the integrated application, in-gym motivation comprises:
transmitting an up-sell opportunity to the portable electronic device to purchase at least one of a session with a personal trainer, an item from a store of the particular fitness center, and a fitness class.

9. The method of claim 1, wherein providing, via the integrated application, in-gym motivation comprises:
transmitting to the portable electronic device at least one of a workout program, a workout video, and an exercise equipment guide.

10. The method of claim 1, wherein providing, via the integrated application, in-gym motivation comprises:
determining the user has accomplished a workout achievement; and
transmitting a notification associated with the workout achievement to at least one member of a social network of the particular fitness center.

11. The method of claim 1, wherein providing, via the integrated application, post-workout motivation comprises:
transmitting to the portable electronic device at least one coupon associated with an item for re-energizing the user.

12. The method of claim 11, wherein transmitting comprises:
determining the user has accomplished at least one workout goal; and
transmitting the at least one coupon in response to determining the uses has accomplished the at least one goal.

13. The method of claim 1, wherein providing, via the integrated application, post-workout motivation comprises:
determining an amount of time since a last visit of the user to the particular fitness center; and
providing a notification to the user through the integrated application of the amount of time.

14. The method of claim 13, wherein providing a notification comprises:
providing an option for at least one of scheduling an appointment with a personal trainer, reserving a spot in a fitness class, and scheduling a visit to the particular fitness center on a calendar application of the user.

15. The method of claim 1, wherein the scheduling function comprises at least one of scheduling a session with a personal fitness trainer of the particular fitness center and reserving a spot in a fitness center class of the particular fitness center.

16. An electronic device operable to interface with a fitness center, the electronic device comprising:
a processor operable to run an integrated application providing functions to:
inform the user of the fitness center;
determine the user has joined the fitness center, and
in response to determining the user has joined the fitness center:
motivate the user to actively attend the fitness center;
provide in-gym motivation when a user is located in the fitness center; and
provide post-workout motivation in response to the user leaving the fitness center, wherein at least one of the functions to motivate the user, to provide in-gym motivation, and to provide post-workout motivation comprises connecting the user, via the integrated application, with a calendar server of the fitness center for allowing the user to perform a scheduling function with the fitness center.

17. The electronic device of claim 16, wherein the electronic device is a portable electronic device.

18. The electronic device of claim 16, further comprising:
communication circuitry operable to receive a listing of available services of the fitness center; and
a display component operable to display the listing.

19. The electronic device of claim 16, further comprising:
display component, and wherein:
the processor is further operable to:
generate a fitness center locator comprising a map and directions to the fitness center; and
direct the display component to display the fitness center locator.

20. The electronic device of claim 16, further comprising:
communication circuitry operable to communicate with at least one piece of equipment of the fitness center to control at least one setting of the at least one piece of equipment.

21. The electronic device of claim 16, further comprising:
a display component; and
communication circuitry operable to:
communicate with at least one piece of equipment of the fitness center to identify past workout information of the user, and wherein:
the processor is further operable to:
generate at least one analytical tool based on the identified past workout information; and
direct the display component to display the analytical tool.

22. Non-transitory machine-readable media for interfacing with a fitness center, the machine-readable media comprising machine-readable instructions recorded thereon for:
introducing a user to a particular fitness center via an integrated application of a portable electronic device, wherein the user is a potential new customer of the particular fitness center;
after the introducing, providing incentive, via the integrated application, for the user to loin the particular fitness center;
in response to the use joining the particular fitness center as a result of the incentive, providing, via the integrated application, in-gym motivation for motivating the user to work out at the particular fitness center; and
providing, via the integrated application, post-workout motivation to encourage the user to actively return to the particular fitness center, wherein at least one of the providing incentive, the providing in-gym motivation, and the providing post-workout motivation comprises connecting the user, via the integrated application, with a calendar server of the particular fitness center for allowing the user to perform a scheduling function with the particular fitness center.

* * * * *